(12) United States Patent
Komiya et al.

(10) Patent No.: US 9,730,577 B2
(45) Date of Patent: Aug. 15, 2017

(54) ENDOSCOPE CLEANING/DISINFECTING APPARATUS AND ENDOSCOPE CLEANING METHOD

(71) Applicant: OLYMPUS CORPORATION, Tokyo (JP)

(72) Inventors: Takaaki Komiya, Hachioji (JP); Hideto Onishi, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 145 days.

(21) Appl. No.: 14/705,467

(22) Filed: May 6, 2015

(65) Prior Publication Data
US 2015/0305608 A1 Oct. 29, 2015

Related U.S. Application Data

(63) Continuation of application No. PCT/JP2013/084108, filed on Dec. 19, 2013.

(30) Foreign Application Priority Data

Dec. 26, 2012 (JP) .................................. 2012-283229

(51) Int. Cl.
| | | |
|---|---|---|
| *B08B 9/00* | (2006.01) | |
| *A61B 1/12* | (2006.01) | |
| *B08B 9/032* | (2006.01) | |
| *A61L 2/18* | (2006.01) | |

(52) U.S. Cl.
CPC .............. *A61B 1/125* (2013.01); *A61B 1/123* (2013.01); *A61L 2/18* (2013.01); *B08B 9/0321* (2013.01); *B08B 9/0325* (2013.01)

(58) Field of Classification Search
CPC ..... A61B 1/123; A61B 1/125; A61L 2/18; B08B 9/0325; B08B 9/0321
USPC ........................................... 134/22.12, 102.1
See application file for complete search history.

(56) References Cited

U.S. PATENT DOCUMENTS

| | | |
|---|---|---|
| 2009/0220377 A1 | 9/2009 | Hasegawa et al. |
| 2012/0118338 A1 | 5/2012 | Nakanishi |

FOREIGN PATENT DOCUMENTS

| | | |
|---|---|---|
| JP | S58-156384 A | 9/1983 |
| JP | S59-069019 A | 4/1984 |
| JP | S62-9843 Y2 | 3/1987 |
| JP | 10-262909 A | 10/1998 |

OTHER PUBLICATIONS

Extended Supplementary European Search Report dated Sep. 27, 2016 in related European Application No. 13 86 7233.2.
International Search Report dated Feb. 10, 2014 issued in PCT/JP2013/084108.

*Primary Examiner* — Eric Golightly
(74) *Attorney, Agent, or Firm* — Scully, Scott, Murphy & Presser, P.C.

(57) ABSTRACT

An endoscope cleaning/disinfecting apparatus includes an endoscope connection section, a liquid supply conduit, a gas feeding conduit, a first gas feeding section, a first exhaust section, and a control section that performs a step of filling the gas feeding conduit with a cleaning liquid, a step of opening the first exhaust section, a step of allowing a gas to flow from the first gas feeding section to the endoscope connection section and feeding a two-phase gas-liquid fluid with which the gas feeding conduit is filled into the conduit of the endoscope and a step of closing the first exhaust section a predetermined time after allowing the gas to flow.

4 Claims, 5 Drawing Sheets

ENDOSCOPE CLEANING/DISINFECTING APPARATUS AND ENDOSCOPE CLEANING METHOD

CROSS REFERENCE TO RELATED APPLICATION

This application is a continuation application of PCT/JP2013/084108 filed on Dec. 19, 2013 and claims benefit of Japanese Application No. 2012-283229 filed in Japan on Dec. 26, 2012, the entire contents of which are incorporated herein by this reference.

BACKGROUND OF THE INVENTION

1. Field of the Invention

The present invention relates to an endoscope cleaning/disinfecting apparatus that cleans/disinfects an endoscope, and an endoscope cleaning method.

2. Description of the Related Art

A configuration of an endoscope cleaning/disinfecting apparatus is well known in which an endoscope conduit is connected to an endoscope connection section of an endoscope cleaning/disinfecting apparatus, and a cleaning liquid is supplied from the endoscope connection section into the endoscope conduit to clean an inside of the endoscope conduit.

Japanese Patent Application Laid-Open Publication No. 58-156384 discloses a configuration of an endoscope cleaning/disinfecting apparatus in which a two-phase gas-liquid fluid which is a mixture of a cleaning liquid and compressed air is supplied into an endoscope conduit from an endoscope cleaning/disinfecting apparatus to remove filth or the like stuck to the inner wall of the endoscope conduit using the gas phase.

Here, a configuration is also well known which is different from Japanese Patent Application Laid-Open Publication No. 58-156384 in which a two-phase gas-liquid fluid is supplied into the endoscope conduit. More specifically, a configuration is well known in which after filling the inside of the endoscope conduit with a liquid, a gas under high pressure is supplied into the endoscope conduit to thereby use liquid removing capability of the gas when removing the liquid from the inside of the endoscope conduit and improve washability in the endoscope conduit rather than simply supplying a gas-liquid mixture into the endoscope conduit.

SUMMARY OF THE INVENTION

An endoscope cleaning/disinfecting apparatus according to one aspect of the present invention is an endoscope cleaning/disinfecting apparatus that cleans/disinfects an endoscope, including an endoscope connection section connected to a conduit of the endoscope, a liquid supply conduit that supplies a cleaning liquid to the conduit of the endoscope via the endoscope connection section, a gas feeding conduit, one end of which is connected to the endoscope connection section and also connected to the liquid supply conduit, a first gas feeding section disposed at the other end of the gas feeding conduit to feed a gas into the conduit of the endoscope via the gas feeding conduit, a first exhaust section provided in the gas feeding conduit, to open, to an atmosphere, the gas feeding conduit, and a control section that performs a step of filling the gas feeding conduit with the cleaning liquid from the liquid supply conduit, a step of opening the first exhaust section, a step of allowing a gas to flow from the first gas feeding section to the endoscope connection section and feeding a two-phase gas-liquid fluid which is a mixture of the cleaning liquid with which the gas feeding conduit is filled and the gas into the conduit of the endoscope and a step of closing the first exhaust section a predetermined time after allowing the gas to flow.

An endoscope cleaning method according to an aspect of the present invention is an endoscope cleaning method using an endoscope cleaning/disinfecting apparatus including an endoscope connection section connected to a conduit of an endoscope, a liquid supply conduit that supplies a cleaning liquid to the conduit of the endoscope via the endoscope connection section, a gas feeding conduit, one end of which is connected to the endoscope connection section and also connected to the liquid supply conduit, and a first gas feeding section disposed at the other end of the gas feeding conduit to feed a gas into the conduit of the endoscope via the gas feeding conduit, the method including a step of filling the gas feeding conduit with the cleaning liquid from the liquid supply conduit, a step of opening the first exhaust section, a step of allowing a gas to flow from the first gas feeding section to the endoscope connection section and feeding a two-phase gas-liquid fluid which is a mixture of the cleaning liquid with which the gas feeding conduit is filled and the gas into the conduit of the endoscope, and a step of closing the first exhaust section a predetermined time after allowing the gas to flow.

DETAILED DESCRIPTION OF THE PREFERRED EMBODIMENTS

Hereinafter, embodiments of the present invention will be described with reference to the accompanying drawings.

Figure 1:
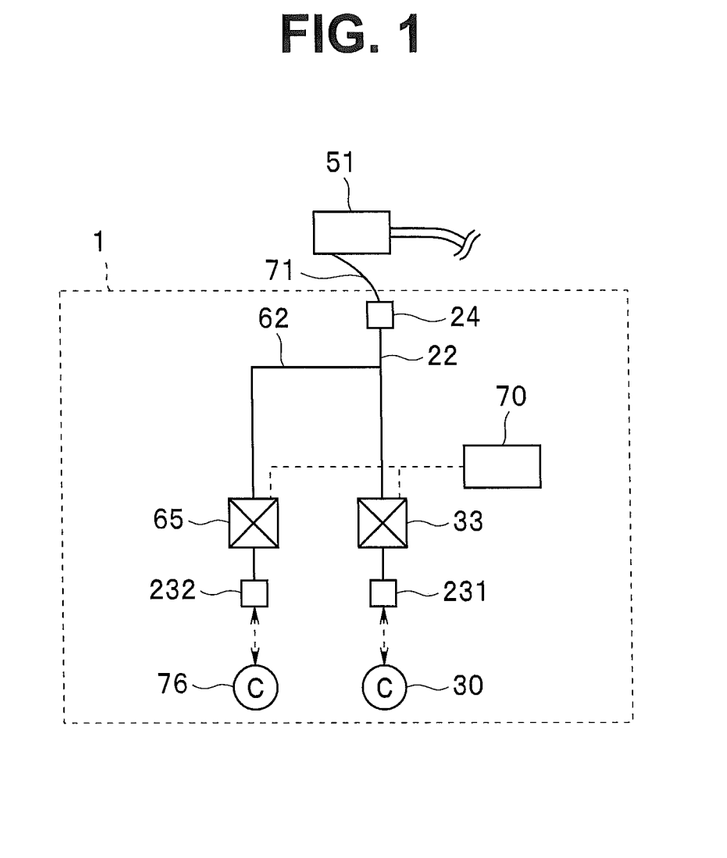
FIG. 1 is a block diagram schematically illustrating a configuration in which an endoscope is connected to an endoscope cleaning/disinfecting apparatus of the present embodiment.

FIG. 1 is a block diagram schematically illustrating a configuration in which an endoscope is connected to an endoscope cleaning/disinfecting apparatus of the present invention. Hereinafter, an overview of a configuration of an endoscope cleaning/disinfecting apparatus 1 of the present embodiment will be described.

The endoscope cleaning/disinfecting apparatus 1 of the present invention has a basic configuration including an endoscope connection section 24 connected to a conduit of an endoscope 51, a gas feeding conduit 22, one end of which is connected to the endoscope connection section 24, a first gas feeding section connection section 231 disposed at the other end of the gas feeding conduit 22 and connected to a first gas feeding section 30 to feed a gas into the conduit of the endoscope 51 via the gas feeding conduit 22, a first valve 33 disposed at a middle position of the gas feeding conduit 22 to allow or block a flow of the gas from the first gas feeding section connection section 231 to the endoscope connection section 24, a connection conduit 62, one end of which is connected to the gas feeding conduit 22, a second gas feeding section connection section 232 disposed at the other end of the connection conduit 22 and connected to a second gas feeding section 76 that feeds the gas into the conduit of the endoscope 51 via the connection conduit 62 and the gas feeding conduit 22, a second valve 65 disposed at a middle position of the connection conduit 62 to allow or block the gas flow from the second gas feeding section connection section 232 to the endoscope connection section 24, and a control section 70 that can control opening/closing of the first valve 33 and the second valve 65 simultaneously.

There is a cleaning method of filling the conduit of the endoscope 51 with a liquid, blowing a gas into the conduit of the endoscope 51 at a blast, causing a liquid-gas mixture to run into the conduit of the endoscope 51 to thereby squeeze filth out of the conduit of the endoscope 51. With this cleaning method, if the gas introduced into the conduit of the endoscope 51 flows below a predetermined flow rate, the liquid filling the conduit runs out without being able to squeeze filth out.

When at least one of the first gas feeding section 30 and the second gas feeding section 76 cannot demonstrate a predetermined output from the start and the output gradually increases, the first valve 33 and the second valve 65 are closed. By switching the first valve 33 and the second valve 65 from a blocked state to a flow state after the first gas feeding section 30 or second gas feeding section 76 reaches the predetermined output, it is possible to implement the aforementioned cleaning method.

The first valve 33 and the second valve 65 may be electromagnetic valves that close a gas channel to thereby allow or block a gas flow or exhaust valves that let a gas out of the conduit to thereby allow or block a gas flow.

Note that the first gas feeding section 30 or the second gas feeding section 76 may be provided in the cleaning/disinfecting apparatus 1 or may be a separate member provided independently of the cleaning/disinfecting apparatus 1.

As methods for filling the conduit of the endoscope 51 with a liquid, the liquid may be manually introduced into the conduit of the endoscope 51 using a syringe or the like or the cleaning/disinfecting apparatus 1 may have a structure for introducing the liquid. One example of a mechanism for introducing the liquid into the conduit of the endoscope 51 is a mechanism using a liquid inlet (circulation port) 11, a liquid supply conduit 12 and a liquid feeding pump 13 shown in FIG. 2.

The control section 70 controls driving of the first valve 33, the second valve 65 and the liquid feeding pump 11, and the cleaning/disinfecting apparatus 1 can thereby automatically implement the above-described cleaning method.

Next, a specific configuration example of the endoscope cleaning/disinfecting apparatus in FIG. 1 will be described.

Figure 2:
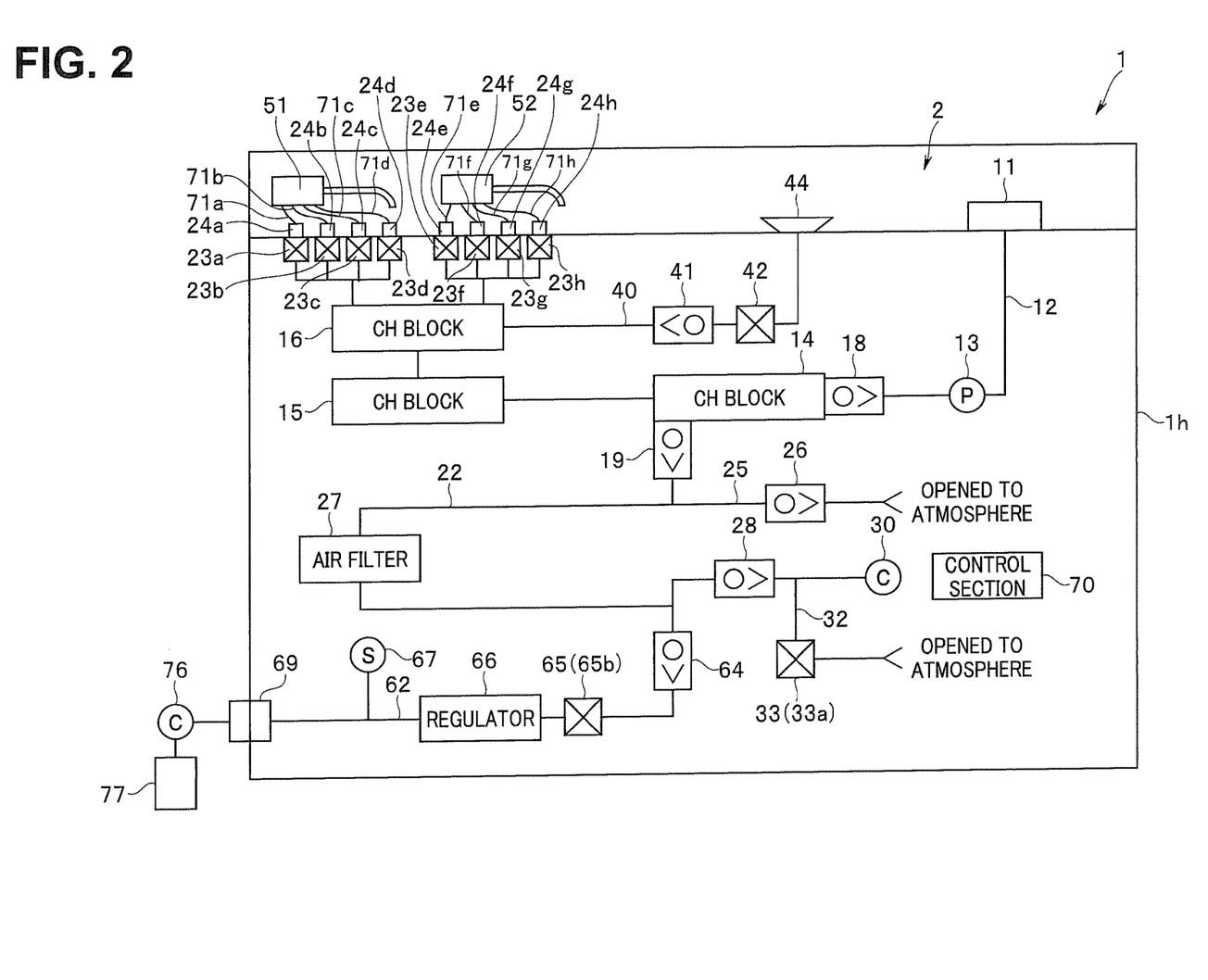
FIG. 2 is a block diagram schematically illustrating a configuration in which a two-phase gas-liquid fluid is supplied into a conduit of the endoscope in the endoscope cleaning/disinfecting apparatus of the present embodiment.

FIG. 2 is a block diagram schematically illustrating a configuration in which a two-phase gas-liquid fluid is supplied into the conduit of the endoscope in the endoscope cleaning/disinfecting apparatus.

Note that in FIG. 2, a configuration will be described by way of example in which the endoscope cleaning/disinfecting apparatus cleans two endoscopes. However, it goes without saying that the number of endoscopes that can be cleaned by the endoscope cleaning/disinfecting apparatus is not limited to 2.

The endoscope cleaning/disinfecting apparatus 1 that cleans/disinfects the conduits of at least the endoscopes 51 and 52 as shown in FIG. 2 is provided with a cleaning/disinfecting tank 2 that can freely accommodate the endoscopes 51 and 52 in an apparatus body 1h.

Endoscope connection sections 24a, 24b, 24c and 24d which are connected to the conduit of the endoscope 51 via tubes 71a, 71b, 71c and 71d are provided at positions facing the cleaning/disinfecting tank 2 of the apparatus body 1h. Note that the number of endoscope connection sections connected to the conduit of the endoscope 51 is not limited to 4.

Similarly, endoscope connection sections 24e, 24f, 24g and 24h which are connected to the conduit of the endoscope 52 via tubes 71e, 71f, 71g and 71h are provided at positions facing the cleaning/disinfecting tank 2 of the apparatus body 1h. Note that the number of endoscope connection sections connected to the conduit of the endoscope 52 is not limited to 4 either.

Furthermore, the endoscope connection section 24a is provided with a channel valve 23a for closing/opening the endoscope connection section 24a and the endoscope connection section 24b is provided with a channel valve 23b for closing/opening the endoscope connection section 24b. The endoscope connection section 24c is provided with a channel valve 23c for closing/opening the endoscope connection section 24c and the endoscope connection section 24d is provided with a channel valve 23d for closing/opening the endoscope connection section 24d.

In this way, a liquid supply into the conduit of the endoscope 51 via the tubes 71a to 71d is switched ON/OFF along with opening/closing of the channel valves 23a to 23d. Note that examples of the liquid include a cleaning liquid, a disinfecting liquid, alcohol, rinse water and a two-phase gas-liquid fluid.

Similarly, the endoscope connection section 24e is provided with a channel valve 23e for closing/opening the endoscope connection section 24e and the endoscope connection section 24f is provided with a channel valve 23f for closing/opening the endoscope connection section 24f. The endoscope connection section 24g is provided with a channel valve 23g for closing/opening the endoscope connection section 24g and the endoscope connection section 24h is provided with a channel valve 23h for closing/opening the endoscope connection section 24h.

In this way, a liquid supply into the conduit of the endoscope 52 via the tubes 71e to 71h is switched ON/OFF along with opening/closing of the channel valves 23e to 23h.

Note that the channel valves 23a to 23h are made up of, for example, freely openable/closable solenoid valves. Opening/closing operations of the channel valves 23a to 23h are controlled by the control section 70 provided in the apparatus body 1h which will be described later.

A gas feeding conduit 22, one end of which is connected to each of the endoscope connection sections 24a to 24h is provided in the apparatus body 1h. A first gas feeding section 30 that feeds a gas into the conduits of the endoscopes 51 and 52 via the gas feeding conduit 22 and each of the endoscope connection sections 24a to 24h is connected to the other end of the gas feeding conduit 22.

Note that the first gas feeding section 30 is made up of, for example, a compressor. The driving of the first gas feeding section 30 is controlled by the control section 70 which will be described later.

Assuming the first gas feeding section 30 as an upstream side, a check valve 28, an air filter 27, a check valve 19, a CH (channel) block 14, a CH block 15 and a CH block 16 are interposed in that order from the upstream side between each of the endoscope connection sections 24a to 24h of the gas feeding conduit 22 and the first gas feeding section 30 in the apparatus body 1h. Note that the CH blocks 14, 15 and 16 all have an inner diameter of 10 mm or more.

The check valve 28 is intended to prevent a gas from flowing from downstream to upstream of the check valve 28, that is, from the air filter 27 side to the first gas feeding section 30 side.

The air filter 27 is intended to remove dust, bacteria or the like in the gas fed from the first gas feeding section 30 and the second gas feeding section 76 which will be described later.

The check valve 19 is intended to prevent a gas or liquid from flowing from downstream to upstream of the check valve 19, that is, from the CH block 14 side to the air filter 27 side.

One end of the liquid supply conduit 12, the other end of which is connected to the circulation port 11 of the cleaning/disinfecting tank 2 is connected to the CH block 14 via a check valve 18. Note that in the present embodiment, the cleaning/disinfecting tank 2 constitutes a liquid supply source.

The check valve 18 is intended to prevent a liquid from flowing from downstream to upstream of the check valve 18, that is, from the CH block 14 side to the circulation port 11 side.

The liquid feeding pump 13 is interposed at a middle position of the liquid supply conduit 12. Note that the driving of the liquid feeding pump 13 is controlled by the control section 70 which will be described later.

Thus, when the channel valves 23a to 23h are opened by the control section 70, a shut-off valve 42 which will be described later is opened, and when the liquid feeding pump 13 is driven, the liquid in the cleaning/disinfecting tank 2 is fed into the conduits of the endoscopes 51 and 52 via the liquid supply conduit 12, the gas feeding conduit 22, the endoscope connection sections 24a to 24h and the tubes 71a to 71h. Note that the liquid supplied into the conduits of the endoscopes 51 and 52 is supplied to the cleaning/disinfecting tank 2 again from the openings of the conduits of the endoscopes 51 and 52.

One end of an atmosphere opening conduit 40, the other end of which is connected to a cleaning case 44 of the cleaning/disinfecting tank 2 so as to be opened to the atmosphere, is connected to the CH block 16.

A first relief valve 41 that is opened when a pressure in the gas feeding conduit 22 becomes a set pressure or higher is interposed at a middle position of the atmosphere opening conduit 40 and the shut-off valve 42 that opens/closes the atmosphere opening conduit 40 under the opening/closing control of the control section 70 which will be described later is interposed downstream of the first relief valve 41.

Note that the set pressure at which the first relief valve 41 opens is set to be smaller than a withstand pressure of the conduits of the endoscopes 51 and 52. For example, when the withstand pressure of the conduits of the endoscopes 51 and 52 is 0.2 MPa, the set pressure is defined as 0.18 MPa. Note that the value of the set pressure is not limited to 0.18 MPa, but can be any value as long as it is smaller than the withstand pressure of the conduits of the endoscopes 51 and 52.

That is, the first relief valve 41 prevents the pressure in the gas feeding conduit 22 from exceeding the withstand pressure of the conduits of the endoscopes 51 and 52. In other words, no gas or liquid having a pressure higher than the withstand pressure is supplied into the conduits of the endoscopes 51 and 52.

One end of an atmosphere opening conduit 32, the other end of which is opened to the atmosphere is connected between the first gas feeding section 30 and the check valve 28 in the gas feeding conduit 22, and a first valve 33 is interposed at a middle position of the atmosphere opening conduit 32.

The first valve 33 is constructed of either a first opening/closing section 33b (not shown in FIG. 2) made up of an electromagnetic valve that opens/closes the gas feeding conduit 22 or a first exhaust section 33a which is made up of an exhaust valve that opens/closes the gas feeding conduit 22 so as to be freely opened to the atmosphere.

On the other hand, when the first valve 33 is made up of an electromagnetic valve, the gas is allowed to flow from the first gas feeding section connection section 231 (see FIG. 1) to the endoscope connection section 24 by opening the electromagnetic valve and a gas flow from the first gas feeding section connection section 231 to the endoscope connection section 24 is blocked by closing the electromagnetic valve.

On the other hand, when the first valve 33 is made up of an exhaust valve, the gas is allowed to flow from the first gas feeding section connection section 231 to the endoscope connection section 24 by closing the exhaust valve and the gas fed from the first gas feeding section connection section 231 is let out of the exhaust valve before arriving at the endoscope connection section 24 by opening the exhaust valve, and the gas flow from the first gas feeding section connection section 231 to the endoscope connection section 24 is thereby blocked.

In the present embodiment, note that description will be given hereinafter assuming that the first valve 33 is the first exhaust section 33a.

That is, when the first exhaust section 33a is open, the gas fed from the first gas feeding section 30 is opened to the atmosphere via the atmosphere opening conduit 32 and when the first exhaust section 33a is closed, the gas is fed toward the downstream side of the gas feeding conduit 22. The opening/closing operation of the first exhaust section 33a is controlled by the control section 70 which will be described later.

One end of the connection conduit 62 is connected between the check valve 28 and the air filter 27 in the gas feeding conduit 22.

The other end of the connection conduit 62 is located outside the apparatus body 1h via an outside air inlet 69 and the second gas feeding section 76 is connected which feeds a predetermined compressed air stored in a tank 77, for example, a gas of 0.8 MPa into the conduits of the endoscopes 51 and 52 via the connection conduit 62 and the gas feeding conduit 22.

Note that the second gas feeding section 76 is constructed of a large-size compressor that can feed a greater volume of gas than, for example, that of the first gas feeding section 30. The second gas feeding section 76 may also be simultaneously connected to another endoscope cleaning/disinfecting apparatus. By so doing, one second gas feeding section 76 is enough even when a plurality of endoscope cleaning/disinfecting apparatuses are installed.

Note that in the present embodiment, the second gas feeding section 76 functions so as to always be driven when power is turned on, not under the operation control of the control section 70.

Thus, when power is on, the gas in the tank 77 is always fed from the second gas feeding section 76, but the second valve 65 which will be described later switches whether or not to supply the gas from the second gas feeding section 76 to the gas feeding conduit 22.

Assuming one end of the connection conduit 62 as the upstream side, a check valve 64, the second valve 65, a regulator 66 and a pressure sensor 67 are interposed in that order from the upstream side between one end and the other end of the connection conduit 62.

The check valve 64 is intended to prevent the gas from flowing from downstream to upstream of the check valve 64, that is, from the gas feeding conduit 22 side to the second valve 65 side.

The second valve 65 is constructed of either a second opening/closing section 65b made up of an electromagnetic valve that opens/closes the connection conduit 62 or a second exhaust section 65a (not shown in FIG. 2) made up of an exhaust valve that opens/closes the connection conduit 62 so as to be freely opened to the atmosphere.

When the second valve 65 is constructed of an electromagnetic valve, the gas is caused to flow from the second gas feeding section connection section 232 to the endoscope connection section 24 by opening the electromagnetic valve or the gas flow from the second gas feeding section connection section 232 to the endoscope connection section 24 is blocked by closing the electromagnetic valve.

On the other hand, when the second valve 65 is constructed of an exhaust valve, the gas is caused to flow from the second gas feeding section connection section 232 to the endoscope connection section 24 by closing the exhaust valve or the gas flow from the second gas feeding section connection section 232 to the endoscope connection section 24 is blocked by opening the exhaust valve since the gas fed from the second gas feeding section connection section 232 is let out of the exhaust valve before the gas arrives at the endoscope connection section 24.

In the present embodiment, note that description will be given hereinafter assuming that the second valve 65 is the second opening/closing section 65b. That is, only when the second opening/closing section 65b is open, the gas fed from the second gas feeding section 76 is fed to the gas feeding conduit 22 side. The opening/closing operation of the second opening/closing section 65b is controlled by the control section 70 which will be described later.

The regulator 66 adjusts the pressure to, for example, 0.2 MPa so as to avoid a high pressure of the gas fed from the second gas feeding section 76 of, for example, 0.8 MPa from being fed into the gas feeding conduit 22 as is and destroying various components, and the pressure sensor 67 is intended to detect the pressure in the connection conduit 62.

One end of an atmosphere opening conduit 25, the other end of which is opened to the atmosphere, is connected between the check valve 19 and the air filter 27 in the gas feeding conduit 22, and a second relief valve 26 that is opened when the pressure in the gas feeding conduit 22 becomes equal to or higher than a set pressure is interposed at a middle position of the atmosphere opening conduit 25.

Note that the set pressure at which the second relief valve 26 is opened is set to be smaller than the withstand pressures of the conduits of the endoscopes 51 and 52 as in the case of the first relief valve 41.

The control section 70 is provided in the apparatus body 1h and is intended to control opening/closing of the shut-off valve 42, the channel valves 23a to 23h, the first valve 33 and the second valve 65, and control the driving of the liquid feeding pump 13 and the first gas feeding section 30.

Note that the control section 70 can control opening/closing of the first valve 33 and control opening/closing of the second valve 65 simultaneously. That is, the present embodiment can control opening/closing of the first exhaust section 33a and control opening/closing of the second opening/closing section 65b simultaneously.

Next, operation of the present embodiment, or more specifically, operation of the control section 70 when cleaning the conduits of the endoscopes 51 and 52 by supplying a two-phase gas-liquid fluid thereinto will be described.

When cleaning the conduits in the endoscopes 51 and 52, the control section 70 performs control to open the channel valves 23a to 23h, control to open the shut-off valve 42 and control to drive the liquid feeding pump 13.

Note that the control section 70 performs control in a first step to keep closed the second opening/closing section 65b which becomes the second valve 65 so that the gas does not flow from the second gas feeding section 76 into the gas feeding conduit 22.

In the first step, when a motor-operated valve or a normally open valve which is closed when powered up is used as the second opening/closing valve, an active operation to close the second opening/closing section 65b is necessary. On the other hand, a normally closed valve which is opened when powered up may also be used as the second opening/closing valve. In this case, an active operation to close the second opening/closing section 65b is unnecessary.

As a result, the cleaning liquid in the cleaning/disinfecting tank 2 is fed into the conduits of the endoscopes 51 and 52 via the circulation port 11, the liquid supply conduit 12, the gas feeding conduit 22, the endoscope connection sections 24a to 24h, and the tubes 71a to 71h.

With the supply of this cleaning liquid, filth or the like stuck to the inner wall of the conduits of the endoscopes 51 and 52 becomes softer. Note that with the supply of the cleaning liquid, clogging in the conduits of the endoscopes 51 and 52 is detected using a flow meter provided in the gas feeding conduit 22, which is not shown.

Next, after feeding the cleaning liquid into the endoscopes 51 and 52 for a set time, the control section 70 executes a second step of performing control to stop the driving of the liquid feeding pump 13 and causing the cleaning liquid to remain in, that is, filling the conduits of the endoscopes 51 and 52, and the gas feeding conduit 22.

After that, the control section 70 executes a third step of performing control to open the first exhaust section 33a, control to close the shut-off valve 42 and further control to drive the first gas feeding section 30.

As a result, the gas fed from the first gas feeding section 30 is opened to the atmosphere via the atmosphere opening conduit 32 because the first exhaust section 33a is open. Note that the feeding pressure of the first gas feeding section 30 at an initial stage of driving is lower than the feeding pressure which becomes a set pressure during normal driving.

After driving the first gas feeding section 30 and after a lapse of a set time at which the feeding pressure of the first gas feeding section 30 becomes a set pressure during normal driving, the control section 70 executes a fourth step of simultaneously performing control to close the first exhaust section 33a and control to open the second opening/closing section 65b which becomes the second valve 65.

As a result, the gas is fed from the first gas feeding section 30 to the gas feeding conduit 22 at the set pressure during normal driving, and at the same time, predetermined compressed air stored in the tank 77 from the second gas feeding section 76 is fed with a pressure adjusted by the regulator 66.

In addition, the gas fed from the first gas feeding section 30 and the second gas feeding section 76 is supplied together with the liquid charged in the gas feeding conduit 22 into the endoscopes 51 and 52 via the endoscope connection sections 24a to 24h and the tubes 71a to 71h. That is, a two-phase gas-liquid fluid is supplied into the conduits of the endoscopes 51 and 52.

In this case, since the liquid in the gas feeding conduit 22 and the conduits of the endoscopes 51 and 52 is removed vigorously by the fed gas, filth or the like stuck to the inner wall of the conduits in the endoscopes 51 and 52 is removed by the liquid removing capability of the gas.

Note that the duration of the gas supply into the conduits of the endoscopes 51 and 52 is preferably set to be longer than the duration of the liquid removing from the conduits of the endoscopes 51 and 52 and the gas feeding conduit 22.

Since the shut-off valve 42 is closed, the first relief valve 41 does not function, but the pressure of the gas fed from the first gas feeding section 30 and second gas feeding section 76 into the gas feeding conduit 22 is prevented from becoming higher than the withstand pressure of the conduits of the endoscopes 51 and 52 by the second relief valve 26 being opened and the gas feeding conduit 22 being opened to the atmosphere as described above. For this reason, no gas having a higher pressure than the withstand pressure is supplied into the conduits of the endoscopes 51 and 52.

Moreover, the control to open the second opening/closing section 65b is performed after the driving of the first gas feeding section 30 because if the control to open the second opening/closing section 65b is performed before the driving of the first gas feeding section 30, the pressure in the gas feeding conduit 22 may increase, which may consequently prevent the first gas feeding section 30 from being driven.

Furthermore, the control to open the second opening/closing section 65b and the control to close the first exhaust section 33a are performed simultaneously because if the control to close the first exhaust section 33a is performed first, as described above, the liquid in the gas feeding conduit 22 and the conduits of the endoscopes 51 and 52 would be removed by the feeding pressure of the first gas feeding section 30 alone, which may prevent sufficient cleaning effects from being obtained.

After feeding the gas, the control section 70 performs control to open the first exhaust section 33a, control to close the second opening/closing section 65b and control to stop the driving of the first gas feeding section 30. As a result, the gas is no longer fed to the gas feeding conduit 22.

After that, when the control section 70 performs control to drive the liquid feeding pump 13, the cleaning liquid in the cleaning/disinfecting tank 2 is supplied again into the conduits of the endoscopes 51 and 52 via the liquid supply conduit 12 and the gas feeding conduit 22 as described above, and the process returns to the normal cleaning step.

Note that the gas may also be supplied to the gas feeding conduit 22 several times in the normal cleaning step. The above-described operation is likewise applicable to a case where the conduit of either endoscope 51 or 52 is cleaned using a two-phase gas-liquid fluid.

Thus, the present embodiment has described that when cleaning the conduits of the endoscopes 51 and 52 using a two-phase gas-liquid fluid, the control section 70 performs control to open the first exhaust section 33a, control to drive the first gas feeding section 30, control to close the first exhaust section 33a when the feeding pressure of the first gas feeding section 30 becomes a set pressure during normal driving, and control to open the second opening/closing section 65b.

Accordingly, the liquid charged into the endoscopes 51 and 52 and the gas feeding conduit 22 is removed vigorously by a high-pressure gas such as the gas from the first gas feeding section 30 or the gas from the second gas feeding section 76. In this way, filth or the like stuck to the inner wall of the conduits in the endoscopes 51 and 52 is more easily removed by the liquid removing capability of the gas.

As described above, it is possible to provide the endoscope cleaning/disinfecting apparatus 1 and the endoscope cleaning method having a configuration capable of improving washability in the endoscope conduit using a two-phase gas-liquid fluid.

Hereinafter, modifications will be described.

The aforementioned present embodiment has shown that in the fourth step, after driving the first gas feeding section 30 and after a lapse of a set time at which the feeding pressure of the first gas feeding section 30 becomes a set pressure during normal driving, the control section 70 performs control to close the first exhaust section 33a and control to open the second opening/closing section 65b simultaneously.

Without being limited to this, when the control section 70 detects the feeding pressure of the first gas feeding section 30 and detects that the feeding pressure of the first gas feeding section 30 becomes a set pressure during normal driving, the control section 70 may perform control to close the first exhaust section 33a which becomes the first valve 33 and control to open the second opening/closing section 65b which becomes the second valve 65 simultaneously.

Figure 3:
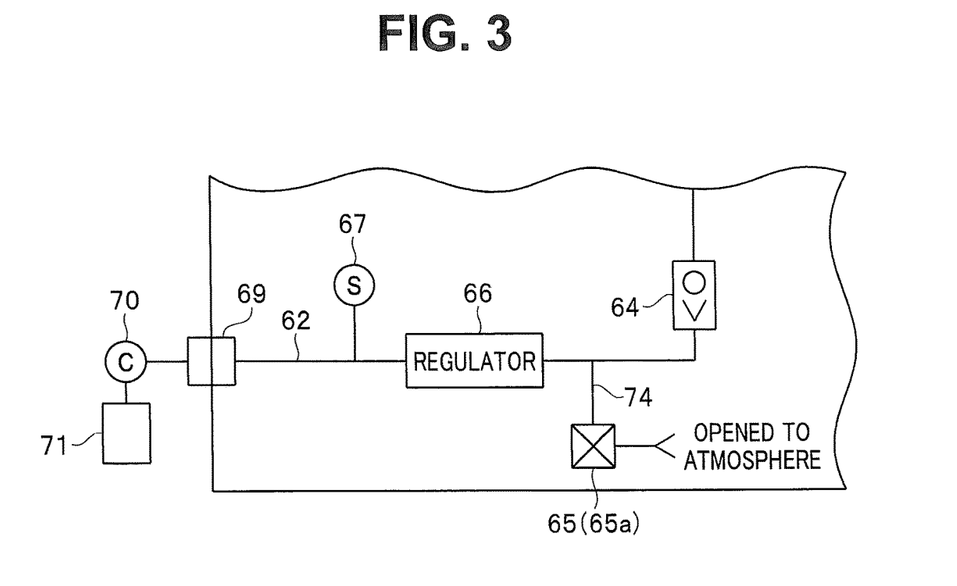
FIG. 3 is a diagram illustrating a modification in which the second valve in FIGS. 1 and 2 is constructed of a second exhaust section.

Hereinafter, a modification will be described using FIG. 3. FIG. 3 is a diagram illustrating a modification in which the second valve in FIG. 1 and FIG. 2 is constructed of a second exhaust section.

The aforementioned present embodiment has shown that the second valve 65 is made up of the second opening/closing section 65b that can freely open/close the connection conduit 62.

Without being limited to this, as shown in FIG. 3, the second valve 65 may be constructed of the second exhaust section 65a which is made of an exhaust valve provided at a middle position of the atmosphere opening conduit 74, one end of which is connected between the regulator 66 of the connection conduit 62 and the check valve 64, and the other end of which is opened to the atmosphere, opening/closing of the second exhaust section 65a being controlled by the control section 70.

Figure 4:
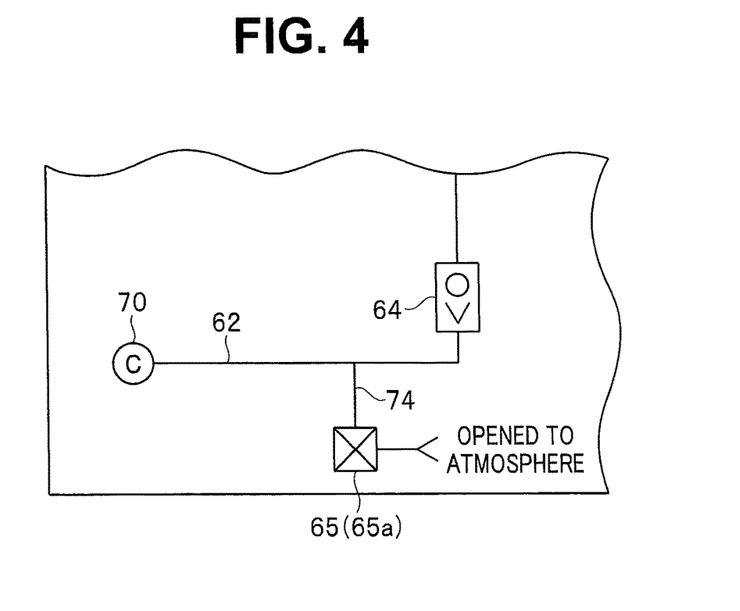
FIG. 4 is a diagram illustrating a modification in which the second gas feeding section in FIG. 3 is provided in the apparatus body.

Hereinafter, another modification will be described using FIG. 4. FIG. 4 is a diagram illustrating a modification in which the second gas feeding section in FIG. 3 is provided in the apparatus body.

As described above, the present embodiment has shown that the second gas feeding section 76 is provided outside the apparatus body 1h, and is constructed of a compressor that feeds a high pressure compressed gas in the tank 77 into the connection conduit 62.

Without being limited to this, as shown in FIG. 4, the second gas feeding section 76 may be provided inside the apparatus body 1h. In this case, a compressor whose feeding pressure is equivalent to that of the first gas feeding section 30 is used for the second gas feeding section 76.

In this configuration, the second valve 65 is constructed of the second exhaust section 65a which is made up of an exhaust valve provided at a middle position of the atmosphere opening conduit 74, one end of which is connected between the second gas feeding section 76 of the connection conduit 62 and the check valve 64, and the other end of which is opened to the atmosphere, opening/closing of the second exhaust section 65a being controlled by the control section 70.

Note that as shown in FIG. 3 and FIG. 4, when the second valve 65 is constructed of the second exhaust section 65a, in the aforementioned first step, the control section 70 performs control to open the second exhaust section 65a to thereby perform control to release the gas fed from the second gas feeding section 76 to the atmosphere via the atmosphere opening conduit 74, and in the fourth step, the control section 70 performs control to close the second exhaust section 65a to thereby perform control to feed the gas fed from the second gas feeding section 76 to the gas feeding conduit 22.

Furthermore, the aforementioned present embodiment has described the second gas feeding section 76 by taking a compressor as an example which is always driven when power is turned on, but without being limited to this, it goes without saying that the second gas feeding section 76 may also be constructed of a compressor that is driven under the driving control of the control section 70.

Figure 5:
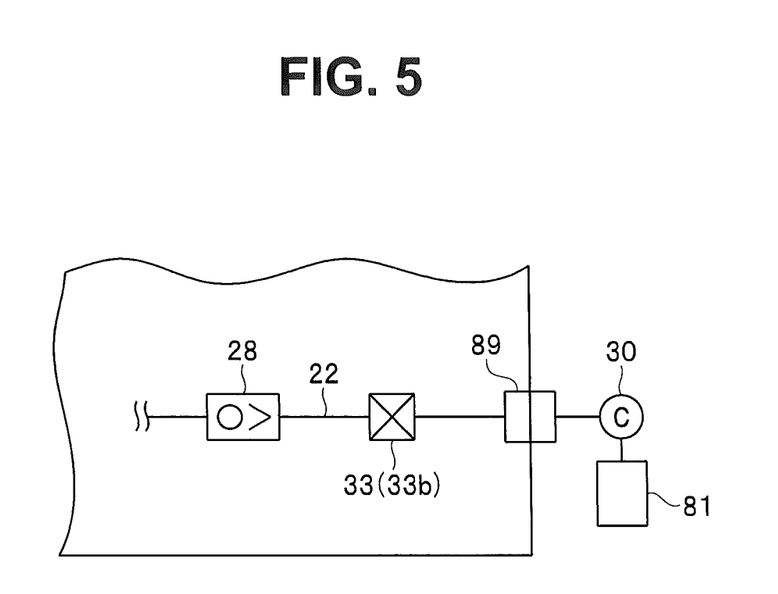
FIG. 5 is a diagram illustrating a modification in which the first gas feeding section in FIGS. 1 and 2 is provided outside the apparatus body.

A further modification will be described using FIG. 5 hereinafter. FIG. 5 is a diagram illustrating a modification in which the first gas feeding section in FIG. 1 and FIG. 2 is provided outside the apparatus body.

The aforementioned present embodiment has shown that the first gas feeding section 30 is provided inside the apparatus body 1h. Without being limited to this, however, as shown in FIG. 5, the first gas feeding section 30 may be provided outside the apparatus body 1h so as to supply a high pressure compressed gas in a tank 81 to the gas feeding conduit 22 via an outside air inlet 89 as in the case of the second gas feeding section 76 of the present embodiment.

In this configuration, the first valve 33 may also be constructed of the first exhaust section 33a shown in the aforementioned present embodiment. Furthermore, it goes without saying that the first valve 33 may also be constructed of the first opening/closing section 33b made up of an opening/closing valve that opens/closes the gas feeding conduit 22 under the control of the control section 70 as shown in, FIG. 5.

Note that as shown in FIG. 5, when the first valve 33 is constructed of the first opening/closing section 33b, in the aforementioned third step, the control section 70 performs control to shut off the supply of the gas fed from the first gas feeding section 30 by closing the first opening/closing section 33b, and in the fourth step, the control section 70 performs to control to supply the gas fed from the first gas feeding section 30 to the gas feeding conduit 22 by opening the first opening/closing section 33b.

A still further modification will be described below. The aforementioned present embodiment has shown that when performing cleaning by supplying a two-phase gas-liquid fluid into the conduits of the endoscopes 51 and 52, the gas is fed from the second gas feeding section 76 provided outside the apparatus body 1h together with the first gas feeding section 30 to the gas feeding conduit 22.

Without being limited to this, cleaning using the two-phase gas-liquid fluid may also be performed by feeding the gas only from the first gas feeding section 30 provided in the apparatus body 1h to the gas feeding conduit 22.

More specifically, as described above, the control section 70 controls to open/close the second valve 65 so that the gas is not fed from the second gas feeding section 76 to the gas feeding conduit 22, stops the driving of the liquid feeding pump 13, charges the liquid into the conduits of the endoscopes 51 and 52 and the gas feeding conduit 22, performs control to close the shut-off valve 42, and further performs control, when the first valve 33 is constructed of, for example, the first exhaust section 33a, to open the first exhaust section 33a.

After that, when the control section 70 performs control to drive the first gas feeding section 30, the gas fed from the first gas feeding section 30 is opened to the atmosphere via the atmosphere opening conduit 32 because the first exhaust section 33a is open. Note that the feeding pressure of the first gas feeding section 30 at this initial stage of driving is lower than a feeding pressure which becomes a set pressure during normal driving.

After driving the first gas feeding section 30 and after a lapse of a set time at which the feeding pressure of the first gas feeding section 30 becomes a set pressure during normal driving, the control section 70 performs control to close the first exhaust section 33a. Note that the control to close the first exhaust section 33a may be performed after detecting the feeding pressure of the first gas feeding section 30 becomes a set pressure during normal driving.

As a result, the gas is fed to the gas feeding conduit 22 from the first gas feeding section 30 not at a weak feeding pressure at the initial stage of driving but at a set pressure during normal driving, and therefore the gas fed from the first gas feeding section 30 is fed into the endoscopes 51 and 52 via the endoscope connection sections 24a to 24h and the tubes 71a to 71h, and the inside of the conduits of the endoscopes 51 and 52 is cleaned by water removing capability of the two-phase gas-liquid fluid as in the case of the present embodiment.

Note that when feeding the gas into the conduits of the endoscopes 51 and 52 from the first gas feeding section 30, since the shut-off valve 42 is closed by the control section 70 as described above, the two-phase gas-liquid fluid never flows through the atmosphere opening conduit 40.

This is because since the atmosphere opening conduit 40 has lower flow resistance than that of the conduits of the endoscopes 51 and 52, if the shut-off valve 42 remains open, the two-phase gas-liquid fluid escapes to the atmosphere opening conduit 40, and it is not possible to supply the two-phase gas-liquid fluid with a sufficient pressure and amount of liquid into the conduits of the endoscopes 51 and 52.

Note that if the shut-off valve 42 is closed, since the second relief valve 26 is opened when the pressure exceeds the set pressure as described above, this will prevent the first relief valve 41 from failing to function, causing the pressure in the gas feeding conduit 22 to become higher than the withstand pressure in the conduits of the endoscopes 51 and 52.

Thus, the configuration using only the first gas feeding section 30 can also appropriately clean the inside of the conduits of the endoscopes 51 and 52 using the two-phase gas-liquid fluid. Note that other effects are similar to those of the aforementioned present embodiment.

Note that the aforementioned present embodiment has described a case where the two endoscopes 51 and 51 are accommodated in the cleaning/disinfecting tank 2 to perform cleaning and a case where the conduits of the two endoscopes 51 and 52 are cleaned using a two-phase gas-liquid fluid as examples, but it goes without saying that the number of endoscopes is not limited to two.

Figure 6:
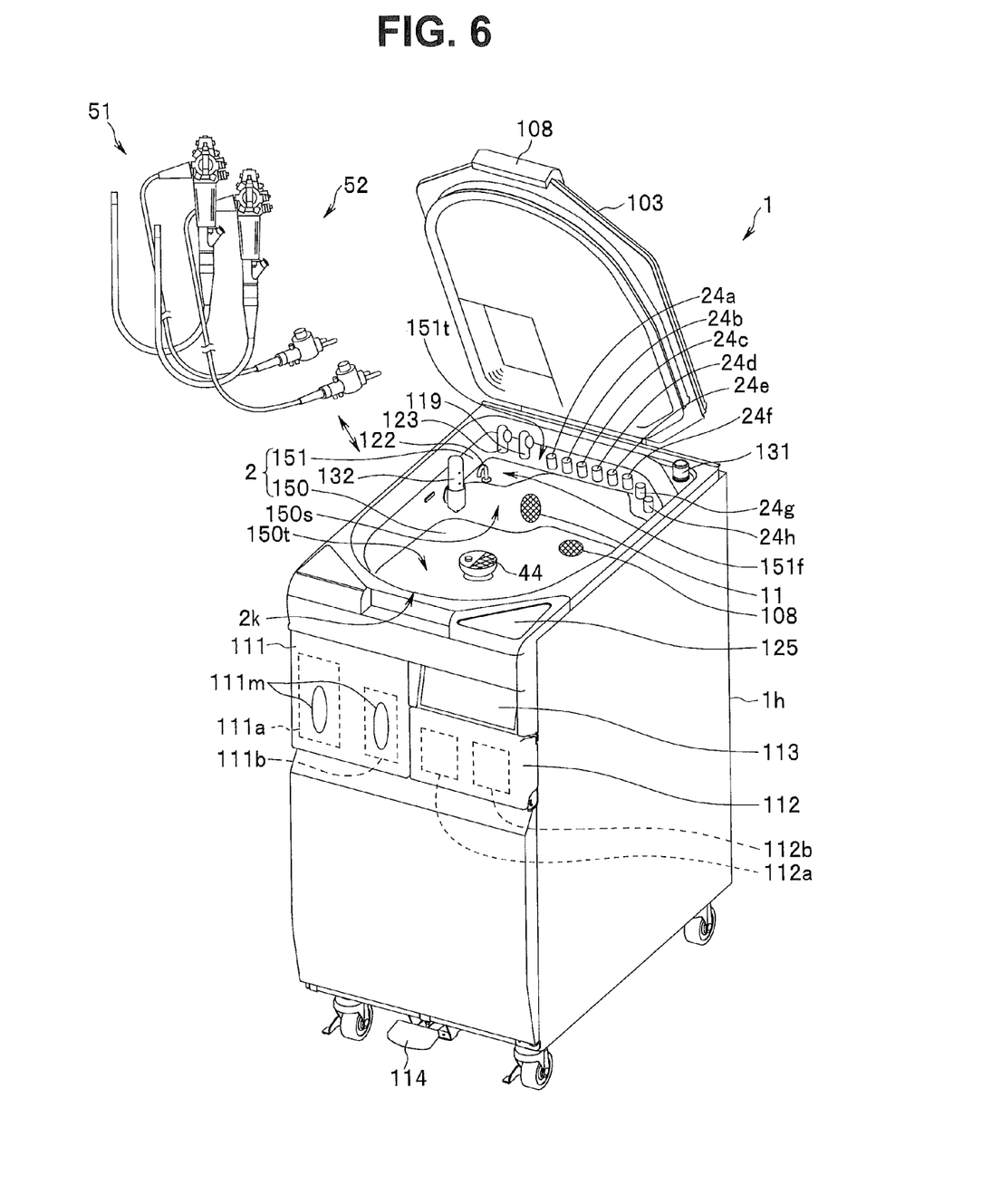
FIG. 6 is a perspective view illustrating an example of the endoscope cleaning/disinfecting apparatus including in the apparatus body, a configuration for detecting clogging of the conduit of the endoscope in FIGS. 1 and 2.

Note that hereinafter, an example of the endoscope cleaning/disinfecting apparatus whose apparatus body 1h has the aforementioned configuration will be described using FIG. 6. FIG. 6 is a perspective view illustrating an example of the endoscope cleaning/disinfecting apparatus whose apparatus body has a configuration of detecting clogging of the conduit of the endoscope in FIG. 1 and FIG. 2.

As shown in FIG. 6, the endoscope cleaning/disinfecting apparatus 1 is an apparatus that cleans and disinfects the two endoscopes 51 and 52 simultaneously, and a main part thereof is constructed of the apparatus body 1h, and a top cover 103 that is a cover connected at the top of the apparatus body 1h in a freely opening/closing manner via, for example, a hinge which is not shown.

Note that when the top cover 103 is placed to cover the apparatus body 1h, the apparatus body 1h and the top cover 103 are kept in a closed position and locked by, for example, a latch 108 disposed at a position where the apparatus body 1h and the top cover 103 face each other.

A detergent/alcohol tray 111 is disposed in a manner freely drawable forward from the apparatus body 1h on the front face in the drawing of the apparatus body 1h in proximity to the operator and at the top of the left half part, for example.

The detergent/alcohol tray 111 accommodates a tank 111a that stores a detergent used to clean the endoscopes 51 and 52 and a tank 111b that stores alcohol which is a liquid used to dry the endoscopes 51 and 52 after cleaning/disinfection, and since the detergent/alcohol tray 111 is freely drawable forward, the liquid can be replenished to a predetermined level to each tank 111a or 111b.

Note that the detergent injected into the tank 111a is a concentrated detergent that is diluted to a predetermined concentration with tap water filtered through a feed water filter which is not shown.

The detergent/alcohol tray 111 is provided with a window section 111m and the operator can check the remaining amount of detergent and alcohol stored in each tank 111a or 111b through the window section 111m.

Furthermore, a cassette tray 112 is disposed on the front of the apparatus body 1h, for example, in an upper part of the right-half section in a manner freely drawable forward of the apparatus body 1h. The cassette tray 112 accommodates a bottle 112a that stores a main agent which is a disinfecting liquid such as peracetic acid which is a liquid used to disinfect the endoscopes 51 and 52 and a bottle 112b that stores a buffer of the main agent, and since the cassette tray 112 is freely drawable, the liquid can be replenished to a predetermined level to the bottles 112a and 112b. Note that a mixture of the main agent and the buffer is called a disinfecting liquid.

Furthermore, a sub-operation panel 113 is disposed on the front of the apparatus body 1h in an upper part of the cassette tray 112 on which a display of the cleaning/disinfecting time and a button for instructing heating of the disinfecting liquid or the like are arranged.

Furthermore, a pedal switch 114 is disposed in a lower part on the front of the apparatus body 1h in the drawing for the operator to step thereon to cause the top cover 103 in the closed position on the apparatus body 1h to open upward of the apparatus body 1h.

Furthermore, a main operation panel 125 is provided on the top surface of the apparatus body 1h near the right end in the drawing on the front side in proximity to the operator, provided with setting switches such as cleaning/disinfecting operation start switch, and cleaning/disinfecting mode selection switch of the apparatus body 1h.

A feed water hose connection port 131 is disposed on the top surface of the apparatus body 1h and on the rear side facing the front in proximity to the operator to supply tap water to the apparatus body 1h to which a feed water hose connected to the faucet is connected. Note that a mesh filter for filtering tap water may also be attached to the feed water hose connection port 131.

Furthermore, the cleaning/disinfecting tank 2 is provided in substantially the center on the top surface of the apparatus body 1h in which the endoscopes 51 and 52 can be freely accommodated, an upward opening endoscope accommodation cavity of which is closed with the top cover 103.

The cleaning/disinfecting tank 2 is constructed of a tank body 150 and a terrace section 151 continuously provided around the outer perimeter of the endoscope accommodation cavity of the tank body 150.

When the endoscopes 51 and 52 after use are cleaned/disinfected, the tank body 150 can freely accommodate the endoscopes 51 and 52 and a bottom surface 150t which is a surface inside the tank of the tank body 150 is provided with an exhaust port 108 to exhaust the cleaning liquid, water, disinfecting liquid or the like supplied to the tank body 150 from the tank body 150.

Furthermore, the circulation port 11 is provided at an arbitrary position on a peripheral side surface 150s which is a surface inside the tank of the tank body 150 to supply the cleaning liquid, water, disinfecting liquid or the like supplied to the tank body 150 into the conduits provid inside the endoscopes 51 and 52 or resupply them from a feed water circulation nozzle 119 to the tank body 150. Note that the circulation port 11 may be provided with a filter for filtering the cleaning liquid, the water or the disinfecting liquid or the like. Note that this circulation port 11 may also be provided in the bottom surface 150t of the tank body 150.

A cleaning case 44 is disposed in substantially the center of the bottom surface 150t of the tank body 150 to accommodate buttons of scope switches or the like of the endoscopes 51 and 52 and forceps plug or the like and clean/disinfect the buttons and the forceps plug or the like together with the endoscopes 51 and 52.

A water level sensor 132 with a cover is provided at an arbitrary position of the side surface 150s of the tank body 150 for detecting the level of the cleaning liquid, water, disinfecting liquid or the like supplied to the tank body 150 to ensure that the liquid is supplied to a set level in the cleaning/disinfecting tank 2.

The terrace section 151 of the cleaning/disinfecting tank 2 is formed by including an inclined surface oriented diagonally upward or more specifically, a circular terrace surface 151t inclined by a defined angle with respect to, for example, the bottom surface 150t of the tank body 150.

A detergent nozzle 122 for supplying a detergent from the detergent tank 111a to the tank body 150 is disposed on a surface other than the terrace surface 151t of the terrace section 151, that is, a surface 151f parallel to the bottom surface 150t of the tank body 150. Note that the detergent nozzle 122 may be disposed on the terrace surface 151t.

A disinfecting liquid nozzle 123 for supplying a disinfecting liquid from a disinfecting liquid tank which is not shown to the tank body 150 is disposed on the terrace surface 151t of the terrace section 151.

Moreover, the feed water circulation nozzle 119 for supplying water to be used for cleaning or rinsing to the tank body 150 or for resupplying the cleaning liquid, water, disinfecting liquid or the like suctioned from the circulation port 11 of the tank body 150 to the tank body 150 is disposed on the terrace surface 151t. Note that the disinfecting liquid nozzle 123 and the feed water circulation nozzle 119 may also be disposed on the parallel surface 151f.

The endoscope connection sections 24a to 24h for supplying a fluid into the conduits of the endoscopes 51 and 52 are provided on the side of the terrace surface 151*t* of the terrace section 151 facing an operator operation position 2*k*.

What is claimed is:

1. An endoscope cleaning/disinfecting apparatus that cleans/disinfects an endoscope comprising:
    an endoscope connection section connected to a conduit of the endoscope;
    a liquid supply conduit that supplies a cleaning liquid to the conduit of the endoscope via the endoscope connection section;
    a gas feeding conduit, one end of which is connected to the endoscope connection section and also connected to the liquid supply conduit;
    a first gas feeding section disposed at the other end of the gas feeding conduit to feed a gas into the conduit of the endoscope via the gas feeding conduit;
    a first exhaust section provided in the gas feeding conduit, to open, to an atmosphere, the gas feeding conduit; and
    a control section that performs a step of filling the gas feeding conduit with the cleaning liquid from the liquid supply conduit, a step of opening the first exhaust section, a step of allowing a gas to flow from the first gas feeding section to the endoscope connection section and feeding a two-phase gas-liquid fluid which is a mixture of the cleaning liquid with which the gas feeding conduit is filled and the gas into the conduit of the endoscope and a step of closing the first exhaust section a predetermined time after allowing the gas to flow.

2. The endoscope cleaning/disinfecting apparatus according to claim 1, further comprising a relief valve provided in the gas feeding conduit that is opened when a pressure in the gas feeding conduit is equal to or higher than a predetermined pressure.

3. An endoscope cleaning method using an endoscope cleaning/disinfecting apparatus the endoscope cleaning/disinfecting apparatus including,
    an endoscope connection section connected to a conduit of an endoscope;
    a liquid supply conduit that supplies a cleaning liquid to the conduit of the endoscope via the endoscope connection section;
    a gas feeding conduit, one end of which is connected to the endoscope connection section and also connected to the liquid supply conduit; and a first exhaust section provided in the gas feeding conduit, to open, to an atmosphere, the gas feeding conduit
    a first gas feeding section disposed at the other end of the gas feeding conduit to feed a gas into the conduit of the endoscope via the gas feeding conduit, the method comprising:
    a step of filling the gas feeding conduit with the cleaning liquid from the liquid supply conduit;
    a step of opening the first exhaust section;
    a step of allowing a gas to flow from the first gas feeding section to the endoscope connection section and feeding a two-phase gas-liquid fluid which is a mixture of the cleaning liquid with which the gas feeding conduit is filled and the gas into the conduit of the endoscope; and
    a step of closing the first exhaust section a predetermined time after allowing the gas to flow.

4. The endoscope cleaning method according to claim 3, further comprising a step of opening a relief valve provided in the gas feeding conduit when a pressure in the gas feeding conduit is equal to or higher than a predetermined pressure.

\* \* \* \* \*